United States Patent [19]

Brookes et al.

[11] 3,991,071

[45] Nov. 9, 1976

[54] FUNGICIDAL COMPOSITIONS CONTAINING SUBSTITUTED IMIDAZOLES

[75] Inventors: Robert F. Brookes, Tollerton; David H. Godson, Chilwell; Anthony F. Hams, Wollaton; David M. Weighton; Wilfred H. Wells, both of Nottingham, all of England

[73] Assignee: The Boots Company Limited, Nottingham, England

[22] Filed: Dec. 13, 1974

[21] Appl. No.: 532,667

Related U.S. Application Data

[63] Continuation-in-part of Ser. No. 477,734, June 10, 1974, abandoned.

[30] Foreign Application Priority Data

June 21, 1973 United Kingdom............... 29535/73

[52] U.S. Cl............................. 260/309; 260/240 R; 424/273
[51] Int. Cl.$^2$........................................ C07D 233/90
[58] Field of Search..................................... 260/309

[56] References Cited

UNITED STATES PATENTS 3,868,458   2/1975   Baker et al. ........................ 260/309

FOREIGN PATENTS OR APPLICATIONS 801,482   10/1973   Belgium

OTHER PUBLICATIONS

Kozlik et al. Chem. Abst. 1973, vol. 79, No. 53327z.
Staab et al. I Chem. Ber. 1962, vol. 95, pp. 1298–1306.
Staab et al. II Chem. Abst. 1962, vol. 57, columns 5864–5865.
Staab et al. III Liebigs Annal. Chem. 1961, vol. 648, pp. 72–82.
Staab et al. IV Chem. Abst. 1962, vol. 57, Cols. 4649–4650.
Tolkmith et al. I Science, 1967, vol. 158, pp. 1462 and 1463.
Tolkmith et al. II World Review of Pest Control, 1967, vol. 6, pp. 74–78.
Zalikin et al. I Chem. Abst. 1971, vol. 75, No. 87741n.
Zalikin et al. II Chem. Abst. 1972, vol. 76, No. 77312e.

*Primary Examiner*—Natalie Trousof
*Attorney, Agent, or Firm*—Lawrence Rosen; E. Janet Berry

[57] ABSTRACT

1-(N,N-disubstituted carbamoyl and thiocarbamoyl)-imidazoles, useful as fungicidal compounds, and their preparation, are described.

7 Claims, No Drawings

FUNGICIDAL COMPOSITIONS CONTAINING SUBSTITUTED IMIDAZOLES

This application is a continuation-in-part of copending application Ser. No. 477,734 filed June 10, 1974, now abandoned.

The invention relates to new compounds having fungicidal properties.

Fungi cause considerable damage to agricultural and horticultural crops and for example attack a wide range of plants. They can be a serious problem in crops causing great economic loss. Although there are fungicidal materials in current use there is always a need for new fungicides of particular use in one or another application.

The compounds of the invention have the general formula

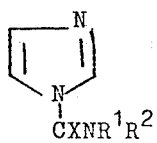

I in which X is oxygen or sulphur, $R^1$ is optionally substituted alkyl, alkenyl, alkynyl, cycloalkyl, phenyl, phenylalkyl, phenylalkenyl, phenoxyalkyl or phenylthioalkyl and $R^2$ is optionally substituted phenyl, phenylalkyl, phenylalkenyl, phenoxyalkyl or phenylthioalkyl, provided that when $R^1$ is methyl or phenyl $R^2$ is substituted phenyl or optionally substituted phenylalkyl, phenylalkenyl, phenoxyalkyl or phenylthioalkyl. It is preferred that X is oxygen.

These compounds have fungicidal activity, especially against mildew, for example powdery mildew (*Erysiphe graminis*) on crops such as wheat, barley and oats. They can also be used to control other fungal diseases of cereal crops such as bunt (*Tilletia caries*) in wheat, loose smut (*Ustilago* spp.) in barley and oats, leaf spot (*Pyrenophora avenae*) in oats, and leaf stripe (*Pyrenophora graminea*) in barley. On horticultural crops control of certain fungi can be obtained, for example powdery mildew (*Podosphaera leucotricha*) and scab (*Venturia inaequalis*) on apple trees, powdery mildew (*Sphaerotheca pannosa*) on roses, and powdery mildew (*Sphaerotheca fuliginea*) on cucurbits such as for example marrows, courgettes, melons and cucumbers. Other fungi which can be controlled include, for example, downy mildew on vine (*Plasmopara viticola*), *Rhizoctonia solani* on crops such as cotton, *Botrytis cinerea* on fruit crops and *Sclerotium rolfsii* on beans. It will be appreciated that not every compound of the invention is uniformly active against all of these fungus species but that a choice must be made of the most appropriate compound for a particular use.

In the above general formula I, $R^1$ can be substituted or unsubstituted alkyl, the alkyl group being straight or branched chain. Preferably the alkyl group contains up to 10 carbon atoms, and typical examples include methyl, ethyl, propyl, isopropyl, n-butyl, isobutyl, sec.-butyl, tert.butyl, n-pentyl, n-hexyl, n-heptyl, n-octyl, n-nonyl, n-decyl. An especially suitable alkyl group is one containing from 1 to 6 carbon atoms. When $R^1$ is substituted alkyl the group can be, for example, any of the alkyl groups listed above substituted with one or more substituents which are the same or different such as, for example, cyano, alkoxy or alkoxycarbonyl. Preferably there is a single substituent which is cyano, ethoxy or ethoxycarbonyl and preferred examples are cyanomethyl, 2-cyanoethyl, 2-ethoxyethyl and ethoxycarbonylmethyl.

As described above the radical $R^1$ can be alkenyl or substituted alkenyl and the alkenyl group, which preferably contains 3 or 4 carbon atoms, can be straight or branched chain. Examples include allyl, 2-methylallyl, 1-propenyl, 3-butenyl, the most preferred groups being allyl and 2-methylallyl. When $R^1$ is substituted alkenyl it can be any one of these alkenyl groups substituted with one or more substituents which are the same or different such as for example halo and in particular chloro. An especially suitable substituted alkenyl group is an alkenyl group containing 3 or 4 carbon atoms substituted with one or two chloro atoms, for example, 2-chloroallyl and 2,3-dichloroallyl.

The group $R^1$ can also be alkynyl or substituted alkynyl in which case it preferably contains 3 to 5 carbon atoms and examples of such groups include pro-2-ynyl and 1,1-dimethylprop-2-ynyl and groups substituted with halogen, especially chlorine, such as for example 4-chlorobut-2-ynyl.

In addition $R^1$ can be substituted or unsubstituted cycloalkyl which preferably contains from 3 to 10 carbon atoms. An especially preferred cycloalkyl group contains 5 to 9 carbon atoms in the ring and is optionally substituted with one to three lower alkyl (especially methyl) groups. Examples include cyclopentyl, cycloheptyl, cyclooctyl, 1-methylcyclohexyl, 1,3-dimethylcyclohexyl and especially cyclohexyl.

The group $R^1$ can also be phenyl, substituted phenyl, phenylalkyl, substituted phenylalkyl, phenylalkenyl, substituted phenylalkenyl, phenoxyalkyl, substituted phenoxyalkyl, phenylthioalkyl or substituted phenylthioalkyl and when the group is substituted it can include a phenyl nucleus with one or more substituents which are the same or different and which are, for example, halo (fluorine, chlorine, bromine and iodine), alkoxy, alkyl, trihalomethyl, cyano, alkylthio, nitro, alkylsulphonyl, acetyl, acetamido, amino or dialkylamino. Preferably there are 1 to 3 substituents which are the same or different and are halo, alkoxy, alkyl, trihalomethyl, cyano, alkylthio, nitro or alkylsulphonyl. A particularly preferred group is substituted with one or two substituents, the same or different, which are halo, alkoxy containing 1 or 2 carbon atoms, alkyl containing 1 to 4 carbon atoms, trifluoromethyl or cyano. Often the substituent or one or more of the substituents is in the 2 or 4 position on the phenyl nucleus.

Typical examples of $R^1$ when it is a substituted phenyl radical are 2-chlorophenyl, 2,4-dichlorophenyl, 2,5-dichlorophenyl, 3,4-dichlorophenyl, 2,4,5-trichlorophenyl, 3-chlorophenyl, 4-chlorophenyl, 2-fluorophenyl, 3-fluorophenyl, 4-fluorophenyl, 4-bromophenyl, 4-iodophenyl, 4-methoxyphenyl, 4-methylthiophenyl, 4-ethoxyphenyl, 2-methylphenyl, 4-methylphenyl, 2,4-dimethylphenyl, 2,5-dimethylphenyl, 4-methylsulphonylphenyl, 3-trifluoromethylphenyl, 4-cyanophenyl, 2-methyl-4-chlorophenyl and 2-chloro-4-nitrophenyl.

When $R^1$ is a phenylalkyl or substituted phenylalkyl radical it can be, for example, optionally substituted benzyl, α-methylbenzyl, phenethyl or higher phenylalkyl radical of the formula $Ph(CH_2)_n$ where $n$ is 3 to 5 such as for example phenylpropyl. Preferably $R^1$ is optionally substituted benzyl or phenethyl and typical examples are benzyl, 2-chlorobenzyl, 4-chlorobenzyl, 2,4-dichlorobenzyl, 3,4-dichlorobenzyl, 4-bromobenzyl, 4-methoxybenzyl, 4-methylbenzyl, 4-nitrobenzyl, 4-cyanobenzyl, phenethyl, 2-chlorophenethyl, 4-chlorophenethyl and 3-methoxyphenethyl.

When $R^1$ is phenylalkenyl or substituted phenylalkenyl it preferably contains from 9 to 11 carbon atoms. More preferably the radical is substituted or unsubstituted 2-phenylallyl or 3-phenylallyl and typical examples include 2-phenylallyl, 2-(2-chlorophenylallyl), 2-(2,4-chlorophenylallyl), 2-(2,4-dichlorophenylallyl), 3-phenylallyl, 3-(2-chlorophenylallyl), 3-(4-chlorophenylallyl) and 3-(2,4-dichlorophenylallyl).

When $R^1$ is a phenoxyalkyl or substituted phenoxyalkyl radical it can be, for example, optionally substituted 2-phenoxyethyl or higher phenoxyalkyl radical of the formula $PhO(CH_2)_n$ where $n$ is 3 to 5 such as for example 3-phenoxypropyl. Preferably $R^1$ is optionally substituted 2-phenoxyethyl and typical examples are 2-phenoxyethyl, 2-(2-chlorophenoxy)ethyl, 2-(4-chlorophenoxy)ethyl, 2-(3-chlorophenoxy)ethyl, 2-(2,4-dichlorophenoxy)ethyl, 2-(4-bromophenoxy)ethyl, 2-(2-methylphenoxy)ethyl, 2-(2-methyl-4-chlorophenoxy)ethyl and 2-(4-methoxyphenoxy)ethyl.

$R^1$ can also be phenylthioalkyl or substituted phenylthioalkyl in which case it can be, for example, an optionally substituted higher phenylthioalkyl radical of the formula $PhS(CH_2)_n$ where $n$ is 3 to 5 but is preferably optionally substituted 2-phenylthioethyl and typical examples are 2-phenylthioethyl, 2-(2-chlorophenylthio)ethyl, 2-(4-chlorophenylthio)ethyl, 2-(3-chlorophenylthio)ethyl, 2-(2,4-dichlorophenylthio)ethyl, 2-(4-bromophenylthio)ethyl, 2-(2-methylphenylthio)ethyl, 2-(2-methyl-4-chlorophenylthio) ethyl and 2-(4-methoxyphenylthio)ethyl.

The radical $R^2$ can be phenyl, substituted phenyl, phenylalkyl, substituted phenylalkyl, phenylalkenyl, substituted phenylalkenyl, phenoxyalkyl, substituted phenoxyalkyl, phenylthioalkyl or substituted phenylthioalkyl, provided that when $R^1$ is methyl or phenyl $R^2$ is substituted phenyl, phenylalkyl, substituted phenylalkyl, phenylalkenyl, substituted phenylalkenyl, phenoxyalkyl, substituted phenoxyalkyl, phenylthioalkyl or substituted phenylthioalkyl. $R^2$ can be any of the groups defined above for $R^1$ when it is phenyl, substituted phenyl, phenylalkyl, substituted phenylalkyl, phenylalkenyl, substituted phenylalkenyl, phenoxyalkyl, substituted phenoxyalkyl, phenylthioalkyl or substituted phenylthioalkyl.

A preferred compound is one of formula I above in which X is oxygen, $R^1$ is optionally substituted alkyl, alkenyl, alkynyl, cycloalkyl, phenyl, phenylalkyl, phenylalkenyl, phenoxyalkyl or phenylthioalkyl and $R^2$ is optionally substituted phenoxyalkyl or phenylthioalkyl. Preferably $R^1$ is alkyl or optionally substituted phenyl or phenylalkyl and $R^2$ is optionally substituted phenoxyalkyl. When the $R^1$ or $R^2$ group is substituted there are most suitably 1 to 3 substituents on the phenyl nucleus which are the same or different and are halo, alkoxy, alkyl, trihalomethyl, cyano, alkylthio, nitro or alkylsulphonyl. When $R^1$ or $R^2$ is substituted phenoxyalkyl it is preferably a substituted 2-phenoxyethyl group. A particularly preferred compound is one in which $R^1$ is alkyl, for example alkyl containing 1 to 6 carbon atoms, and $R^2$ is 2-phenoxyethyl optionally substituted with 1 to 3 substituents which are the same or different and are methoxy, methyl, trihalomethyl and especially halo.

A further preferred compound of the invention is one that has the general formula

  II in which X is oxygen or sulphur, $R^1$ is alkyl containing 1 to 5 carbon atoms; alkenyl containing 3 or 4 carbon atoms optionally substituted with one or two chloro atoms; phenyl optionally substituted with one or more substituents selected from halo, nitro, alkoxy containing 1 or 2 carbon atoms, alkyl containing 1 or 2 carbon atoms or trifluoromethyl; benzyl; or cyclohexyl; and $R^2$ is phenyl optionally substituted with one or more substituents selected from halo, nitro, alkoxy containing 1 or 2 carbon atoms, alkyl containing 1 or 2 carbon atoms or trifluoromethyl; or benzyl optionally substituted with one or more substituents selected from halo, nitro, alkoxy containing 1 or 2 carbon atoms, alkyl containing 1 or 2 carbon atoms or trifluoromethyl; provided that when $R^1$ is methyl or phenyl $R^2$ is substituted phenyl or optionally substituted benzyl. An especially preferred compound is one in which, in formula II above, X is oxygen, $R^1$ is alkyl containing 1 to 4 carbon atoms and $R^2$ is phenyl substituted with one or two halo atoms. A further preferred compound is one in which, in formula II above, X is oxygen, $R^1$ is alkyl containing 1 to 4 carbon atoms and $R^2$ is benzyl substituted with one or two halo atoms.

The invention also includes a fungicidal composition which comprises a compound of formula I together with a diluent or carrier. More than one compound of the invention can, of course, be included in the composition. In addition the composition can comprise one or more additional active ingredients, for example compounds known to possess herbicidal, fungicidal, insecticidal or acaricidal properties. Additional fungicides suitable for instance in fruit-crop applications, include for example dodine, captan, dithianon and benomyl. It is sometimes desirable, especially when spraying fruit or vegetable crops, to include an insecticide or acaricide, for instance an organochlorine compound such as for example DDT, benzene hexachloride or dicofol; an organophosphorus compound such as for example fenitrothion, azinphos-methyl, demeton or dimethoate; or a carbamate such as for example carbaryl.

The diluent or carrier in the composition of the invention can be a solid or a liquid optionally in association with a surface-active agent, for example, a dispersing agent, emulsifying agent or wetting agent. Suitable surface-active agents include anionic compounds such as a carboxylate for example a metal carboxylate of a long chain fatty acid; an N-acylsarcosinate; a sulphonate such as for example an alkylbenzenesulphonate or a petroleum sulphonate; a sulphate such as for example a sulphated alcohol, a sulphated natural fat or oil; or a phosphate ester such as for example an alkyl orthophosphate or an alkyl polyphosphate. Nonionic surface-active agents include for example an ethoxylated alkylphenol such as a nonyl phenoxypoly(ethyleneoxy)ethanol; an ethoxylated aliphatic alcohol such as an alkylpoly(ethyleneoxy) ethanol; or a carboxylic ester solubilised with a polyol or polyoxyethylene. Examples of a cationic surface-active agent include, for instance, an aliphatic mono-, di-, or polyamine as an acetate, naphthenate or oleate; an oxygen-containing amine such as amine oxide or polyoxyethylene alkylamine; an amide-linked amine prepared by the condensation of a carboxylic acid with a di- or polyamine; or a quaternary ammonium salt.

The composition of the invention can take any form known in the art for the formulation of fungicidal compounds, for example, a solution, a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

As a dispersion, the composition comprises a compound of the invention dispersed in a liquid medium, preferably water. It is often convenient to supply the consumer with a primary composition which can be diluted with water to form a dispersion having the desired concentration. The primary composition can be provided in any one of the following forms. It can be a dispersible solution which comprises a compound of the invention dissolved in a water-miscible solvent with the addition of a dispersing agent. Alternatively it can be a dispersible powder which comprises a compound of the invention and a dispersing agent. A further alternative comprises a compound of the invention in the form of a finely ground powder in association with a dispersing agent and intimately mixed with water to give a paste or cream which can if desired be added to an emulsion of oil in water to give a dispersion of active ingredient in an aqueous oil emulsion.

An emulsion comprises a compound of the invention dissolved in a water-immiscible solvent which is formed into an emulsion with water in the presence of an emulsifying agent. An emulsion of the desired concentration can be formed from a primary composition of the following types. A concentrated stock emulsion can be supplied comprising a compound of the invention in combination with an emulsifying agent, water and a water-immiscible solvent. Alternatively an emulsifiable concentrate cand be supplied to the user comprising a solution of a compound of the invention in a water-immiscible solvent containing an emulsifying agent.

A dusting powder comprises a compound of the invention intimately mixed and ground with a solid pulverulent diluent, for example, kaolin.

A granular solid comprises a compound of the invention associated with a similar diluents to those which may be employed in dusting powders, but the mixture is granulated by known methods. Alternatively it comprises the active ingredient absorbed or adsorbed on a pre-formed granular diluent, for example, fuller's earth attapulgite or limestone grit.

The concentration of the active ingredient in the composition of the present invention is preferably within the range of 0.001 to 10 percent by weight, especially 0.005 to 5 percent by weight. In a primary composition the amount of active ingredient can vary widely and can be, for example, from 5 to 95 percent by weight of the composition.

Also included in the invention is a method of controlling a phytopathogenic fungus which comprises applying to seeds, plants or their habitat a compound of the general formula:

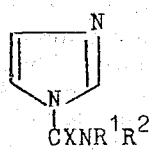

in which X is oxygen or sulphur, $R^1$ is optionally substituted alkyl, alkenyl, alkynyl, cycloalkyl, phenyl, phenylalkyl, phenylalkenyl, phenoxyalkyl or phenylthioalkyl and $R^2$ is optionally substituted phenyl, phenylalkyl, phenylalkenyl, phenoxyalkyl or phenylthioalkyl. For convenience and effectiveness it is preferred to apply the active compound in the form of a composition as described above.

In the method of the invention the compound is applied to seeds, plants or their habitat. Thus the compound can be applied directly to the soil before, at or after drilling so that the active compound can be absorbed by the roots of the plant or so that the presence of active compound in the soil can control the growth of fungi which attack the seed. When the soil is treated directly the active compound can be applied in any manner which allows it to be intimately mixed with the soil such as by spraying, by broadcasting a solid in the form of granules, or by applying the active ingredient at the same time as drilling by inserting it in the same drill as the seeds. A suitable application rate is within the range of from 0.05 to 20 lb. per acre, more preferably from 0.1 to 10 lb. per acre.

Alternatively the active compound can be applied directly to the plant by, for example, spraying or dusting either at the time when the fungus has begun to appear on the plant, or before the appearance of fungus as a protective measure. In both such cases the preferred mode of application is by foliar spraying. It is generally important to obtain good control of fungi in the early stages of plant growth as this is the time when the plant can be most severely damaged. For cereal crops such as wheat, barley and oats it is often desirable to spray the plant at or before growth stage 5 although additional treatments by spraying when the plant is more mature can augment resistance to the growth or spread of fungi. The spray or dust can conveniently contain a pre- or post- emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.01 to 10 lb. per acre. preferably from 0.05 to 5 lb. per acre.

In a further method of the invention the active compound can be applied to the seed as a dressing or slurry in order to combat seed-borne diseases. This method is of particular use in the treatment of cereal grain against attack by, for example, leaf spot of oats, leaf stripe of barley, loose smut of barley, loose smut of oats, and bunt of wheat. If cereal grain is to be stored in a storeroom or container it is sometimes convenient to treat the store-room or container with the active compound instead of, or in addition to, treatment of the cereal grain itself. A suitable rate of application for a seed dressing is from 0.05 to 5oz. per bushel, such as for example from 0.1 to 2oz. per bushel.

A particular method of the invention is one for controlling powdery mildew on a cereal crop, such as for example wheat, barley, oats or rye which comprises applying to the crop or the soil in which the crop is grown a compound of the general formula I. For a particular compound it is necessary to choose the most effective method for amongst those described above at a suitable rate of application that ensures fungus control but avoids any adverse effect on the plant.

The compounds of the invention can be prepared by a process which comprises reacting imidazole with a carbamoyl halide or thiocarbamoyl halide of the general formula z—$CXNR^1R^2$ (IV) in which $R^1$, $R^2$ and X are as defined above in formula I and Z is halogen, for example chlorine or bromine and preferably chlorine. The reaction is suitably effected in the presence of an inert organic liquid as the reaction medium, which is preferably a solvent for the reactants. Preferably the reaction 15 carried out in the presence of a suitable acid-binding agent, for example a tertiary amine such as triethylamine or pyridine or an excess of imidazole reactant, in order to absorb the hydrogen halide produced in the reaction. Alternatively it can be carried out by first forming an alkali metal derivative of imidazole, for example an N-sodio-derivative, and subsequently reacting it with the carbamoyl or thiocarbamoyl halide. The reaction can be carried out at a temperature of for example from 0° to 200° C., preferably within the range of 50° to 150° C.

The carbamoyl halide or thiocarbamoyl halide of the general formula IV can be prepared by reacting a secondary amine of general formual $HNR^1R^2$ with a carbonyl halide or thiocarbonyl halide of the general formula $CXZ_2$. The secondary amine $HNR^1R^2$ can, in its turn, be prepared in accordance with any of the methods well known in the art. For example it can be made by reacting a primary amine or the formula $R^1NH_2$ or $R^2NH_2$ with the respective alkyl halide of the formula $R^2Q$ or $R^1Q$, in which Q is halogen, preferably bromine.

A further method of preparing the compounds of the invention comprises reacting carbonylbisimidazole or thiocarbonylbisimidazole of the general formula:

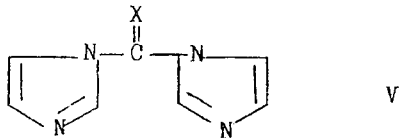

V with a secondary amine of the general formula $HNR^1R^2$, in which X, $R^1$ and $R^2$ are as defined above in formula I. The reaction is suitably effected in the presence of an inert organic liquid as the reaction medium, which is preferably a solvent for the reactants, at a temperature of, for example, from 0° to 100° C.

The compound of formula V can be prepared by reacting imidazole with about 0.5 molecular proportions, or less, of a carbonyl halide or thiocarbonyl halide of the formula $CXZ_2$ in which Z is halogen, preferably chlorine, in accordance with known methods. The reaction is preferably performed in the presence of a suitable acid-binding agent, for example a tertiary amine such as triethylamine or pyridine or excess imidazole, and at a temperature of, for example, from −20° to 50° C. After formation of the carbonylbisimidazole or thiocarbonylbisimidazole it is often convenient to react it, without isolation, with the amine reactant $HNR^1R^2$.

The compounds of the present invention can also be prepared by a process which comprises reacting a carbamoyl halide or thiocarbamoyl halide of the general formula

VI with a secondary amine of the general formula $HNR^1R^2$, in which X, $R^1$ and $R^2$ are as defined above in formula I and Z is halogen for example chlorine or bromine and preferably chlorine. The reaction is suitably effected in the presence of an inert organic liquid as the reaction medium, which is preferably a solvent for the reactants. Preferably the reaction is carried out in the presence of a suitable acid-binding agent, for example a tertiary amine such as triethylamine or pyridine or an excess of imidazole reactant, in order to absorb the hydrogen halide produced in the reaction. The compound of formula VI can be made by reacting imidazole with a carbonyl halide or thiocarbonyl halide of the formula $CXZ_2$ in accordance with known methods.

The invention is illustrated by the following examples.

In the tabulated compounds the following abbreviations are used: Ph=phenyl, Me=methyl, ET=ethyl, Pr=propyl, Bu=butyl, i=iso and s=secondary. Alkyl radicals without the designations i- or s- signify normal radicals.

The physical constant for a solid compound is its melting point and for a liquid the physical constant is the boiling point at the stated pressure (mm. Hg).

EXAMPLE 1

This example illustrates the preparation of compounds according to the invention.

44g. of N-2-chlorophenyl-N-propylcarbamoyl chloride, 14g. off imidazole and 30 ml. triethylamine were refluxed in 200 ml. of dry tetrahydrofuran for 5 hours. The reaction mixture was poured into 2 liters of water and the slurry chilled causing some separation from the aqueous phase. A slightly sticky crystalline solid was collected, washed with water and dried in vacuo. It was recrystallised from a mixture of toluene and light petroleum (62°–68° C. fraction) with charcoaling. On cooling, an oil separated which soon solidified to give the product, 1-(N-2-chlorophenyl-N-propylcarbamoyl-)imidazole m.p. 75.5°–76.5° C.

The N-21-chlorophenyl-N-propylcarbamoyl chloride was prepared in the following way.

A solution of 255g. 2-chloroacetanilide in 900 ml. dry tetrahydroffuran was added to a water-cooled stirred suspension of 75g. sodium hydride (50 percent w/w) in the same solvent. When the evolution of hydrogen had ceased, the mixture was stirred for 10 minutes and 140 ml. propyl bromide was added dropwise. The mixture was refluxed for two hours before 50 ml. propyl bromide was added and the heating was continued for another 16 hours. The precipitate of sodium bromide was collected and washed with dry tetrahydrofuran. Evaporation of the organic filtrate gave an oil which was heated under refux with 750 ml. concentrated hydrochloric acid and 750 ml. industrial methylated spirits for 46 hours. Further additions of 250 ml. and 125 ml. portions of concentrated hydrochloric acid were made after 19 and 27 hours heating respectively.

The organic solvents were removed under reduced pressure and the cooled acid solution was basified with concentrated sodium hydroxide solution. The organic layer was isolated by ether extraction and the dried ether solution evaporated to give an oil. Distillation gave 2-chloro-N-propylaniline as the oily product, boiling point 89°–92° C./3.0 mm. Hg.

22g. of this product was dissolved in 100 ml. ethyl acetate and added to a quantity of 150 ml. ethyl acetate through which a stream of phosgene was passed at reflux temperature. Passage of phosgene was continued for 1½ hours after addition was completed. Evaporation of the ethyl acetate gave an oil which was distilled, b.p. 132°–133° C./3.0 mm. Hg. This was N-2-chlorophenyl-N-propylcarbamoyl chloride.

The following carbamoylimidazole compounds of general formula I (X=oxygen) were prepared in a similar manner. Crude liquids were distilled under vacuum to give the pure product.

| $R^1$ | $R^2$ | Physical State | Constant |
|---|---|---|---|
| Et | 2Cl—Ph | liquid | 148–149° C./0.5 mm. |
| Et | 4Cl—Ph | solid | 44–47° C. |
| Me | 3Cl—Ph | solid | 80–82° C. |
| Pr | 4Cl—Ph | liquid | 152–154° C./0.25 mm |
| Et | 3Cl—Ph | solid | 67–69° C. |
| Pr | 4Br—Ph | solid | 57–59° C. |
| Me | 3,4diCl—Ph | solid | 87–89° C. |
| Pr | 3Cl—Ph | solid | 64–66° C. |
| Pr | 3,4diCl—Ph | solid | 70–71° C. |
| Et | 3,4diCl—Ph | solid | 82–83° C. |
| Et | 4F—Ph | solid | 52.5–53.5° C. |
| Me | 2F—Ph | solid | 66.5–68.5° C. |
| Me | 3F—Ph | solid | 65.5–67.5° C. |
| Et | 2F—Ph | solid | 53.5–55° C. |
| Pr | 2F—Ph | solid | 67–68.5° C. |
| Pr | 3F—Ph | solid | 36–38° C. |
| Pr | 4F—Ph | liquid | 134° C./0.1 mm. |
| Me | 2,5diCl—Ph | solid | 102–104.5° C. |
| Et | 2,5diCl—Ph | solid | 108–110° C. |
| Bu | 4Cl—Ph | liquid | 154–156° C./0.15 mm. |
| Me | 4I—Ph | solid | 177.5–179° C. |
| Me | 4F—Ph | solid | 73–74° C. |
| Pentyl | 4Cl—Ph | solid | 49–50° C. |
| Et | 3F—Ph | solid | 72–74° C. |
| Pr | 2,5diCl—Ph | solid | 106–108° C. |
| Bu | 4F—Ph | solid | 59–61° C. |
| Hexyl | 4Cl—Ph | liquid | 170–171° C./0.2 mm. |
| i-Bu | 4Cl—Ph | solid | 76.5–78.5° C. |
| Bu | 2Cl—Ph | solid | 89.5–91° C. |
| Et | 2,4diCl—Ph | solid | 70.5–72° C. |
| Me | 2,4diCl—Ph | solid | 87.5–89.5° C. |
| i-Pr | 4Cl—Ph | solid | 78–79° C. |
| Pr | 2,4diCl—Ph | solid | 82–83° C. |
| s-Bu | 4Cl—Ph | liquid | 147–149° C./0.08 mm. |
| i-Pr | 2Cl—Ph | solid | 78–79.5° C. |
| s-Bu | 2Cl—Ph | solid | 70.5–72° C. |
| i-Bu | 2Cl—Ph | solid | 70.5–72° C. |
| Bu | 3Cl—Ph | liquid | 149–150° C./0.05 mm. |
| Allyl | 4Cl—Ph | solid | 55–56.5° C. |
| Pentyl | 2Cl—Ph | liquid | 174–175° C./0.4 mm. |
| Hexyl | 2Cl—Ph | liquid | 185° C./0.6 mm. |
| Pentyl | 2,4diCl—Ph | liquid | 176–178° C./0.4 mm. |
| Bu | 2,4diCl—Ph | liquid | 165–166° C./0.15 mm. |
| Bu | 2F—Ph | liquid | 140–141° C./0.2 mm. |
| Pentyl | 2F—Ph | liquid | 153° C./0.3 mm. |
| Hexyl | 2F—Ph | liquid | 156–157° C./0.15 mm. |
| Me | 4Cl—Ph | solid | 110–112° C. |
| Me | 4F—Ph | solid | 53–55° C. |
| Me | 2Cl—Ph | liquid | 140–142° C./0.4 mm. |
| Et | 4Br—Ph | solid | 58–60° C. |
| Pr | 2Br—Ph | solid | 93–95° C. |
| Me | 2,4,5triCl—Ph | solid | 144–5–146° C. |
| CNCH₂CH₂ | Ph | solid | 90–91° C. |
| i-Pr | Ph | solid | 47–49° C. |
| Pentyl | Ph | liquid | 139–140° C./0.15 mm. |
| Pr | 4Me—Ph | liquid | 142–144° C./0.25 mm. |
| Hexyl | Ph | liquid | 153–157° C./0.3 mm. |
| Octyl | Ph | liquid | 165–168° C./0.2 mm. |
| Et | 4MeO—Ph | solid | 103.5–104.5° C. |
| Hexadecyl | Ph | solid | 58–60° C. |
| Et | CF₃—Ph | solid | 79.5–80.5° C. |
| Et | 2Me—Ph | solid | 66–68° C. |
| Octadecyl | Ph | solid | 66–67° C. |
| s-Bu | Ph | solid | 53–55° C. |
| i-Bu | Ph | solid | 87–89° C. |
| Me | 4Bu—Ph | liquid | 154–156° C./0.2 mm. |
| Decyl | Ph | liquid | 182° C./0.15 mm. |
| Me | 4EtO—Ph | liquid | 150–152° C./0.1 mm. |
| Allyl | 2Me—Ph | liquid | 138–139° C./0.2 mm. |
| Nonyl | Ph | liquid | 176–177° C./0.1 mm. |
| Undecyl | Ph | liquid | 192–194° C./0.2 mm. |
| Pr | 4EtO—Ph | liquid | 160° C./0.15 mm. |
| Me | 2Me—4Cl—Ph | solid | 122–124° C. |
| Me | 2,4diMe—Ph | solid | 81–82.5° C. |
| Et | 2Me—4Cl—Ph | solid | 61–63° C. |
| Et | 2,4,5triCl—Ph | solid | 111–113° C. |
| Bu | 4Me—Ph | liquid | 143–144° C./0.1 mm. |
| Me | 2,5diMe—Ph | solid | 70.5–72° C. |
| Me | 2MeO—Ph | solid | 85–86.5° C. |
| Et | 2,5diMe—Ph | solid | 75–77° C. |
| tert.Bu | Ph | solid | 68–70° C. |
| Me | 2,5diMe—Ph | solid | 70.5–72° C. |
| EtCO₂CH₂ | 4Cl—Ph | solid | 129.5–131° C. |
| Et | 2,5diMe—Ph | solid | 75–77° C. |
| Me | 3,4diMe—Ph | solid | 99–101° C. |
| Me | 3MeO—Ph | solid | 89–90.5° C. |
| Me | 3,5diMe—Ph | solid | 127–128.5° C. |
| Pr | 2,5diMe—Ph | solid | 57–59° C. |
| Et | 3Cl—4Me—Ph | solid | 87–89° C. |
| Pr | 3Cl—4Me—Ph | liquid | 180° C./1 mm. |
| Bu | 3Cl—4Me—Ph | liquid | 184–186° C./1 mm. |
| Me | 4i—Pr—Ph | liquid | 160–161° C./0.5 mm. |
| Et | 4i—Pr—Ph | liquid | 155° C./0.5 mm. |
| Bu | 4i—Pr—Ph | liquid | 166° C./0.4 mm. |
| Pr | 4i—Pr—Ph | liquid | 161–162° C./0.5 mm. |
| CNCH₂ | 3,4diCl—Ph | solid | 152–154° C. |
| CNCH₂ | 2Me—4Cl—Ph | solid | 132–134° C. |
| Bu | 2Me—4Cl—Ph | solid | 41–43° C. |
| Bu | 2Me—Ph | liquid | 149–151° C./0.3 mm. |
| Bu | 3Me—Ph | liquid | 153–154° C./0.3 mm. |
| CNCH₂CH₂ | 4Cl—Ph | solid | 108–110° C. |
| Pr | 2Me—Ph | liquid | 139–141° C./0.2 mm. |
| CNCH₂CH₂ | 2Cl—Ph | liquid | 200–202° C./0.25 mm. |
| Bu | 3,4,5triCl—Ph | liquid | 190–192° C./0.2 mm. |
| Pr | 3,4,5triCl—Ph | solid | 143–145° C. |
| Pr | 4tert.Bu—Ph | liquid | 159–160° C./0.3 mm. |
| Et | 2Br—4Me—Ph | liquid | 163–166° C./0.25 mm. |
| Me | 4CN—Ph | solid | 145–147° C. |
| Me | 4MeSO₂—Ph | solid | 138–140° C. |
| Et | Ph | solid | 44–46° C. |
| Bu | Ph | solid | 25° C. |
| Me | 4Me—Ph | solid | 118–120° C. |
| Me | 3CF₃—Ph | solid | 72–73° C. |
| Pr | Ph | solid | 44–46° C. |
| Pr | 3CF₃—Ph | liquid | 128–129° C./0.2 mm. |
| Et | 2,4diMe—Ph | liquid | 132–134° C./0.2 mm. |
| Et | 4CN—Ph | solid | 124° C. |
| Cyclohexyl | Ph | solid | 77–79° C. |
| Ph | 4F—Ph | solid | 104–106° C. |
| Ph | 4Me—Ph | solid | 110–112° C. |
| Ph | 3Cl—Ph | solid | 138–140° C. |
| Ph | 4MeO—Ph | solid | 95–97° C. |
| Ph | 4MeS—Ph | solid | 82–84° C. |
| Ph | 3CF₃—Ph | solid | 115–117° C. |

Intermediates

The following carbamoyl chloride intermediates of general formula R¹R²NCOCl were prepared in a similar way to the method described above for the preparation of N-2-chlorophenyl-N-propylcarbamoyl chloride.

| $R^1$ | $R^2$ | Physical State | Constant |
|---|---|---|---|
| Et | 2Cl—Ph | liquid | 122–123° C./3.0 mm. |

-continued

| R¹ | R² | Physical State | Constant |
|---|---|---|---|
| Et | 4Cl—Ph | liquid | 134–135° C./2.3 mm. |
| Me | 3Cl—Ph | solid | 84–87° C. |
| Pr | 4Cl—Ph | liquid | 147–148° C./5.0 mm. |
| Et | 3Cl—Ph | solid | 63–64° C. |
| Pr | 4Br—Ph | liquid | 108–110° C./2.5 mm. |
| Me | 3,4diCl—Ph | solid | 43.5–45.5° C. |
| Pr | 3Cl—Ph | liquid | 132–133° C./3.0 mm. |
| Pr | 3,4diCl—Ph | solid | 40–42° C. |
| Et | 3,4diCl—Ph | solid | 60–61.5° C. |
| Et | 4F—Ph | liquid | 112–114° C./4.5 mm. |
| Me | 2F—Ph | liquid | 101–102° C./4.0 mm. |
| Me | 3F—Ph | solid | 73.5–74.5° C. |
| Et | 2F—Ph | liquid | 98–100° C./4.5 mm. |
| Pr | 2F—Ph | liquid | 120° C./4.5 mm. |
| Pr | 3F—Ph | liquid | 114–116° C./3.5 mm. |
| Pr | 4F—Ph | solid | 41–42.5° C. |
| Me | 2,5diCl—Ph | solid | 71–73° C. |
| Et | 2,5diCl—Ph | liquid | 145–147° C./4.0 mm. |
| Bu | 4Cl—Ph | liquid | 150° C./2.25 mm. |
| Me | 4I—Ph | solid | 122–123.5° C. |
| Me | 4F—Ph | solid | 55–57° C. |
| Pentyl | 4Cl—Ph | liquid | 121° C./0.3 mm. |
| Et | 3F—Ph | solid | 38–39° C. |
| Pr | 2,5diCl—Ph | solid | 55.5–57° C. |
| Bu | 4F—Ph | liquid | 110° C./1.5 mm. |
| Hexyl | 4Cl—Ph | liquid | 127° C./0.3 mm. |
| i-Bu | 4Cl—Ph | liquid | 148° C./5.0 mm. |
| Bu | 2Cl—Ph | liquid | 127° C./1.8 mm. |
| Et | 2,4diCl—Ph | liquid | 129–132° C./2.5 mm. |
| Me | 2,4diCl—Ph | solid | 49.5–51.5° C. |
| i-Pr | 4Cl—Ph | solid | 83–84° C. |
| Pr | 2,4diCl—Ph | liquid | 157–159° C./5.8 mm. |
| s-Bu | 4Cl—Ph | liquid | 149° C./4.5 mm. |
| i-Pr | 2Cl—Ph | solid | 60–61.5° C. |
| s-Bu | 2Cl—Ph | liquid | 128–129° C./2.0 mm. |
| i-Bu | 2Cl—Ph | liquid | 129–130° C./2.5 mm. |
| Bu | 3Cl—Ph | liquid | 135° C./2.0 mm. |
| Allyl | 4Cl—Ph | liquid | 101° C./0.1 mm. |
| Pentyl | 2Cl—Ph | liquid | 118–120° C./0.05 mm. |
| Hexyl | 2Cl—Ph | liquid | 133–134° C./0.35 mm. |
| Pentyl | 2,4diCl—Ph | liquid | 131–133° C./0.25 mm. |
| Bu | 2,4diCl—Ph | liquid | 130–133° C./0.1 mm. |
| Bu | 2F—Ph | liquid | 105–106° C./0.15 mm. |
| Pentyl | 2F—Ph | liquid | 116–117° C./0.2–0.25 mm. |
| Hexyl | 2F—Ph | liquid | 114–115° C./0.1 mm. |
| Me | 4Cl—Ph | solid | 64–67° C. |
| Me | 4F—Ph | solid | 55–57° C. |
| Me | 2Cl—Ph | solid | 47–50° C. |
| Et | 4Br—Ph | solid | 43.5–45° C. |
| Me | 2,4,5triCl—Ph | solid | 48–49° C |
| CNCH₂CH₂ | Ph | liquid | 130–132° C./0.15 mm. |
| i-Pr | Ph | solid | 89–91° C. |
| Pentyl | Ph | liquid | 144–146° C./5.5 mm. |
| Pr | 4Me—Ph | liquid | 84–86° C./0.15 mm. |
| Hexyl | Ph | liquid | 106° C./0.3 mm. |
| Octyl | Ph | liquid | 124–126° C./0.2 mm. |
| Et | 4MeO—Ph | solid | 65–66.5° C. |
| Hexadecyl | Ph | liquid | 198–200° C./0.15 mm. |
| Et | CF₃—Ph | liquid | 108–110° C./2.5 mm. |
| Et | 2Me—Ph | liquid | 114–115° C./4.0 mm. |
| Octadecyl | Ph | solid | 42.5–43.5° C. |
| s-Bu | Ph | liquid | 120–122° C./3.0 mm. |
| i-Bu | Ph | liquid | 115–116° C./2.5 mm. |
| Me | 4Bu—Ph | liquid | 157–158° C./5.0 mm. |
| Decyl | Ph | liquid | 132–134° C./0.1 mm. |
| Me | 4EtO—Ph | solid | 66–68° C. |
| Allyl | 2Me—Ph | liquid | 115–116° C./1.5 mm. |
| Nonyl | Ph | liquid | 132–133° C./0.15 mm. |
| Undecyl | Ph | liquid | 150–151° C./0.2 mm. |
| Pr | 4EtO—Ph | liquid | 165° C./3.5 mm. |
| Me | 2Me—4Cl—Ph | solid | 44–45.5° C. |
| Me | 2,4diMe—Ph | liquid | 108° C./2.5 mm. |
| Et | 2Me—4Cl—Ph | liquid | 128–129° C./2.5 mm. |
| Et | 2,4,5triCl—Ph | liquid | 120–121° C./0.3 mm. |
| Bu | 4Me—Ph | liquid | 130–131° C./2.0 mm. |
| Me | 2,5diMe—Ph | liquid | 108° C./2.5 mm. |
| Me | 2MeO—Ph | liquid | 133° C./4.0 mm. |
| tert.Bu | Ph | solid | 85–86° C. |
| Me | 2,5diMe—Ph | solid | 44.5–46.5° C. |
| EtCO₂CH₂ | 4Cl—Ph | solid | 48.5–50° C. |
| Et | 2,5diMe—Ph | liquid | 83° C./0.1 mm. |
| Me | 3,4diMe—Ph | solid | 62–63.5° C. |
| Me | 3MeO—Ph | solid | 89–90.5° C. |
| Me | 3,5diMe—Ph | solid | 64–66° C. |
| Pr | 2,5diMe—Ph | liquid | 129° C./3.0 mm. |
| Et | 3Cl—4Me—Ph | solid | 55–57° C. |
| Bu | 3Cl—4Me—Ph | liquid | 184–186° C./1.0 mm. |
| Me | 4i—Pr—Ph | liquid | 114–116° C./0.6 mm. |

-continued

| R¹ | R² | Physical State | Constant |
|---|---|---|---|
| Et | 4i—Pr—Ph | liquid | 109–111° C./0.3 mm. |
| Bu | 4i—Pr—Ph | liquid | 124–126° C./0.4 mm. |
| Pr | 4i—Pr—Ph | liquid | 120° C./0.5 mm. |
| CNCH₂ | 3,4diCl—Ph | liquid | 158° C./0.1 mm. |
| CNCH₂ | 2Me—4Cl—Ph | liquid | 148–150° C./0.4 mm. |
| Bu | 2Me—4Cl—Ph | liquid | 134–136° C./0.9–1.0 mm. |
| Bu | 2Me—Ph | liquid | 104–107° C./0.2 mm. |
| Bu | 3Me—Ph | liquid | 97–99° C./0.15 mm. |
| CNCH₂CH₂ | 4Cl—Ph | solid | 118.5–120° C. |
| Pr | 2Me—Ph | liquid | 104–108° C./0.4 mm. |
| CNCH₂CH₂ | 2Cl—Ph | liquid | 144–145° C./0.2 mm. |
| Bu | 3,4,5triCl—Ph | liquid | 134–136° C./0.05 mm. |
| Pr | 3,4,5triCl—Ph | solid | 71–73° C. |
| Pr | 4 tert.Bu—Ph | liquid | 122° C./0.1 mm. |
| Et | 2Br—4Me—Ph | liquid | 120–122° C./0.2 mm. |
| Me | 4CN—Ph | solid | 108–110° C. |
| Me | 4MeSO₂—Ph | solid | 119–121° C. |
| Et | Ph | solid | 46–48° C. |
| Bu | Ph | liquid | 165–168° C./20 mm. |
| Me | 4Me—Ph | solid | 68–70° C. |
| Me | 3CF₃—Ph | liquid | 82–84° C./0.3 mm. |
| Pr | Ph | solid | 45–46° C. |
| Pr | 3CF₃—Ph | liquid | 121–123° C./5.5 mm. |
| Et | 2,4diMe—Ph | liquid | 83° C./0.1 mm. |
| Et | 4CN—Ph | solid | 98–100° C. |
| Cyclohexyl | Ph | solid | 72–74° C. |
| Ph | 4F—Ph | solid | 82–84° C. |
| Ph | 4Me—Ph | solid | 95–96° C. |
| Ph | 3Cl—Ph | liquid | 130° C./0.2 mm. |
| Ph | 4MeO—Ph | solid | 56–58° C. |
| Ph | 4MeS—Ph | solid | 95–97° C. |
| Ph | 3CF₃—Ph | solid | 53–54° C. |

EXAMPLE 2

Compounds of the Invention

In a similar way to that described in example 1 the following carbamoylimidazole compounds of general formula I (X=oxygen) were prepared.

| R¹ | R² | Physical State | Constant |
|---|---|---|---|
| Me | 4MeO—Ph | solid | 49–51° C. |
| Heptyl | 3Cl—4Me—Ph | liquid | 198–200° C./0.4 mm. |
| Decyl | 2Cl—Ph | liquid | 227–230° C./0.3 mm. |
| Pr | 2NO₂—4Cl—Ph | solid | 116–118° C. |
| Allyl | 2Cl—Ph | solid | 70.5–72° C. |
| Pr | 2Cl—4NO₂—Ph | solid | 91–93° C. |
| Pr | 4MeO—Ph | liquid | 170–172 C./0.5 mm. |
| 2-Methyl-allyl | 4Cl—Ph | liquid | 144–146° C./0.05 mm. |
| 2,3di-chloroallyl | 4Cl—Ph | liquid | 180–182° C./0.1 mm. |
| Bu | 4Bu—Ph | liquid | 175–177° C./0.5 mm. |
| Pr | 4Bu—Ph | liquid | 162–164° C./0.2 mm. |
| Pr | 2Cl—5CF₃—Ph | solid | 105–107° C. |
| Bu | 2Cl—5CF₃—Ph | liquid | 156° C./0.6 mm. |
| Me | 2NO₂—4-MeO—Ph | solid | 86–88° C. |
| EtOCH₂CH₂ | 4Cl—Ph | liquid | 151–153° C./0.05 mm. |
| 4Cl—PhCH₂ | 2,4diCl—Ph | solid | 90–92° C. |
| 2,4diCl—PhCH₂ | Ph | solid | 72–74° C. |
| PhCH₂ | 2,4diCl—Ph | liquid | 210–213° C./0.5 mm. |
| 4Br—Ph | 4Br—Ph | solid | 149–150° C. |
| 4Cl—PhCH₂ | 4Cl—Ph | solid | 134.5–135.5° C. |
| PhCH₂ | 4Cl—Ph | solid | 59.5–61° C. |
| 4Me—PhCH₂ | 4Me—Ph | solid | 107–109° C. |
| 2,4diCl—PhCH₂ | 4Cl—Ph | solid | 144–146° C. |
| 4Me—Ph | 4Me—Ph | solid | 137–138.5° C. |
| PhCH₂ | 4MeO—Ph | solid | 90–92° C. |
| 4Me—PhCH₂ | 2,4diCl—Ph | solid | 78–81° C. |
| Ph | PhCH₂CH₂ | solid | 97–99° C. |
| 4Cl—Ph | PhCH₂CH₂ | solid | 84–85° C. |
| Me | 2Cl—4NO₂—Ph | solid | 151–153° C. |
| 2,4diCl—Ph | PhCH₂CH₂ | solid | 115–117° C. |
| Pentyl | 2Cl—4NO₂—Ph | solid | 76–78° C. |

Intermediates

In a similar way to that described in example 1 the following carbamoyl chloride intermediates of general formula R¹R²NCOCl were prepared.

| R¹ | R² | Physical State | Constant |
|---|---|---|---|
| Me | 4MeO—Ph | solid | 43–45° C. |
| Heptyl | 3Cl—4Me—Ph | liquid | 150–153° C./0.3 mm. |
| Decyl | 2Cl—Ph | liquid | 154–156° C./0.1 mm. |
| Pr | 2NO₂—4Cl—Ph | not isolated | |
| Allyl | 2Cl—Ph | liquid | 121–122° C./2.0 mm. |
| Pr | 2Cl—4NO₂—Ph | not isolated | |
| Pr | 4MeO—Ph | liquid | 152–154° C./2.5 mm. |
| 2-Methylallyl | 4Cl—Ph | liquid | 95–96° C./0.05 mm. |
| 2,3dichloroallyl | 4Cl—Ph | solid | 42–44.5° C. |
| Bu | 4Bu—Ph | liquid | 123—124° C./0.05–0.1 mm. |
| Pr | 4Bu—Ph | liquid | 124–126° C./0.05 mm. |
| Pr | 2Cl—5CF₃—Ph | liquid | 96–98° C./0.1 mm. |
| Bu | 2Cl—5CF₃—Ph | liquid | 105–106° C./0.05 mm. |
| Me | 2NO₂—4-MeO—Ph | not isolated | |
| EtOCH₂CH₂ | 4Cl—Ph | not isolated | |
| 4Cl—PhCH₂ | 2,4diCl—Ph | liquid | 172–176° C./0.2–0.3 mm. |
| 2,4diCl—PhCH₂ | Ph | solid | 78–80° C. |
| PhCH₂ | 2,4diCl—Ph | liquid | 186° C./0.8 mm. |
| 4 Br—Ph | 4 Br—Ph | solid | 127–128.5° C. |
| 4Cl—PhCH₂ | 4Cl—Ph | solid | 68.5–69.5° C. |
| PhCH₂ | 4Cl—Ph | solid | 69–70° C. |
| 4Me—PhCH₂ | 4Me—Ph | liquid | 150–152° C./0.1 mm. |
| 2,4diCl—PhCH₂ | 4Cl—Ph | solid | 81–83° C. |
| PhCH₂ | 4MeO—Ph | liquid | 162–165° C./0.1 mm. |
| 4Me—PhCH₂ | 2,4diCl—Ph | liquid | 146–148° C./0.1 mm. |
| Ph | PhCH₂CH₂ | solid | 68–70° C. |
| 4Cl—Ph | PhCH₂CH₂ | solid | 83–85° C. |
| Me | 2Cl—4NO₂—Ph | not isolated | |
| 2,4diCl—Ph | PhCH₂CH₂ | solid | 87–89° C. |
| Pentyl | 2Cl—4NO₂—Ph | not isolated | |

EXAMPLE 3

This example illustrates the preparation of compounds according to the invention.

A mixture of 12.3 g. N-4-chlorobenzyl-N-propylcarbamoyl chloride and 6.8 g. imidazole was refluxed in 75 ml. dry tetrahydrofuran for a period of five hours. The filtered reaction mixture was evaporated and the product dissolved in ether. After washing with water the ethereal solution was dried and evaporated. Addition of light petroleum and cooling gave a solid which was separated and recrystallised from a mixture of toluene and light petroleum. The product, 1-(N-4-chlorobenzyl-N-propylcarbamoyl)imidazole had a melting point 89°–91° C.

The N-4-chlorobenzyl-N-propylcarbamoyl chloride was prepared in the following way.

A solution of 48.3 g. 4-chlorobenzyl chloride in 40 ml. acetonitrile was added to a mixture of 18 g. propylamine, 12.6 g. sodium hydroxide, 50 ml. acetonitrile and 30 ml. water. The mixture was shaken intermittently for 45 minutes. An exothermic reaction occurred and a white solid separated in the lower phase. After a period of 4 days the reaction mixture was poured into a liter of water and the organic phase isolated with ether. Distillation of the ethereal extract gave an oily product N-4-chlorobenzyl-N-propylamine, b.p. 101°–106° C./1.7–2.5 mm. Hg.

A solution of 25.2 g. N-4-chlorobenzyl-N-propylamine in 150 ml. ethyl acetate was added to 150 ml. ethyl acetate under reflux whilst phosgene was passed through. The passage of phosgene was continued for 2½ hours, after which the ethyl acetate was evaporated to give an oily product. Distillation gave N-4-chlorobenzyl-N-propylcarbamoyl chloride, an oil b.p. 162°–164° C./4.0 mm. Hg.

The following carbamoylimidazole compounds of general formula I (X=oxygen) were prepared in a similar manner. Crude liquids were distilled under vacuum to give the pure product.

Compounds of the Invention

| R¹ | R² | Physical State | Constant |
|---|---|---|---|
| Me | 3,4di-Cl—PhCH₂ | solid | 68–69° C. |
| Me | 2,4di-Cl—PhCH₂ | solid | 105–107° C. |
| Me | 4Cl—PhCH₂ | solid | 60–62° C. |
| Me | 2MeO—PhCH₂ | solid | 111–112.5° C. |
| Et | 4Cl—PhCH₂ | solid | 57–59° C. |
| i-Pr | PhCH₂ | solid | 48–50° C. |
| Bu | 4Cl—PhCH₂ | solid | 58–60° C. |
| Pr | 4Cl—PhCH₂ | solid | 89–91° C. |
| Et | 4NO₂—PhCH₂ | solid | 107–109° C. |
| Pr | 4NO₂—PhCH₂ | solid | 83.5–85° C. |
| i-Pr | 4Cl—PhCH₂ | solid | 120–121.5° C. |
| i-Pr | 4—NO₂—PhCH₂ | solid | 189.5–191° C. |
| Pr | 2,4di-Cl—PhCH₂ | solid | 119–121° C. |
| Allyl | 2,4di-Cl—PhCH₂ | solid | 123–125° C. |
| Bu | 2,4di-Cl—PhCH₂ | solid | 80–82° C. |
| i-Pr | 2,4di-Cl—PhCH₂ | solid | 102–104° C. |
| Et | 2,4di-Cl—PhCH₂ | solid | 119–121° C. |
| i-Bu | 2,4di-Cl—PhCH₂ | liquid | 194° C./0.5 mm. |
| Et | 2Cl—PhCH₂ | solid | 81–83° C. |
| Allyl | 2Cl—PhCH₂ | solid | 73–75° C. |
| Allyl | 4Cl—PhCH₂ | liquid | 180–181° C./0.35 mm. |
| Me | 4MeO—PhCH₂ | solid | 66–68° C. |
| i-Pr | 2Cl—PhCH₂ | liquid | 170–172° C./0.25 mm. |
| Pr | 3,4di-Cl—PhCH₂ | solid | 106–108° C. |

Compounds of the Invention (continued)

| R¹ | R² | Physical State | Constant |
|---|---|---|---|
| Allyl | 3,4diCl—PhCH₂ | solid | 97–99° C |
| Pr | 2Cl—PhCH₂ | liquid | 163–165° C./0.1 mm. |
| PhCH₂ | PhCH₂ | solid | 62–63.5° C. |

Intermediates

The following carbamoyl choride intermediates of general formula R¹R²NCOCl were prepared in a similar way to the method described above for the preparation of N-4-chlorobenzyl-N-propylcarbamoyl chloride.

| R¹ | R² | Physical State | Constant |
|---|---|---|---|
| Me | 3,4diCl—PhCH₂ | solid | 49–50° C. |
| Me | 2,4diCl—PhCH₂ | liquid | 118° C./0.2 mm. |
| Me | 4Cl—PhCH₂ | solid | 46–48° C. |
| Et | 4Cl—PhCH₂ | liquid | 152–153° C./3.5 mm. |
| i-Pr | PhCH₂ | liquid | 146–147° C./6.5 mm. |
| Bu | 4Cl—PhCH₂ | liquid | 173–174° C./3.5 mm. |
| Pr | 4Cl—PhCH₂ | liquid | 162–164° C./4.0 mm. |
| Et | 4NO₂—PhCH₂ | liquid | 154–155° C./0.15 mm. |
| Pr | 4NO₂—PhCH₂ | liquid | 158–159° C./0.3 mm. |
| i-Pr | 4Cl—PhCH₂ | liquid | 120–121° C./0.3 mm. |
| i-Pr | 4NO₂—PHCH₂ | solid | 83–84° C. |
| Pr | 2,4diCl—PhCH₂ | liquid | 138–140° C./0.1 mm. |
| Allyl | 2,4diCl—PhCH₂ | liquid | 138–140° C./0.1 mm. |
| Bu | 2,4diCl—PhCH₂ | liquid | 148–150° C./0.4 mm. |
| i-Pr | 2,4diCl—PhCH₂ | liquid | 128–130° C./0.1 mm. |
| Et | 2,4diCl—PhCH₂ | liquid | 130–132° C./0.3 mm. |
| i-Bu | 2,4diCl—PhCH₂ | liquid | 154–156° C./0.4 mm. |
| Et | 2Cl—PhCH₂ | liquid | 124–126° C./1.0 mm. |
| Allyl | 2Cl—PhCH₂ | liquid | 136–138° C./1.5 mm. |
| Allyl | 4Cl—PhCH₂ | liquid | 141–142° C./1.8 mm. |
| Me | 4MeO—PhCH₂ | liquid | 140–141° C./1.4 mm. |
| Me | 2Cl—PhCH₂ | liquid | 110° C./0.4 mm. |
| i-Pr | 2Cl—PhCH₂ | liquid | 132–134° C./1.0 mm. |
| Pr | 3,4diCl—PhCH₂ | liquid | 158–160° C./0.3 mm. |
| Allyl | 3,4diCl—PhCH₂ | liquid | 148–150° C./0.1 mm. |
| Pr | 2Cl—PhCH₂ | liquid | 138–140° C./1.5 mm. |
| PhCH₂ | PhCH₂ | liquid | 154–158° C./0.4 mm. |

EXAMPLE 4

Compounds of the Invention

In a similar way to that described in example 3 the following carbamoylimidazole compounds of general formula I (X=oxygen) were prepared

| R¹ | R² | Physical State | Constant |
|---|---|---|---|
| Bu | PhCH₂ | liquid | 171–172° C./0.4 mm. |
| Cyclopentyl | 2,4diCl—PhCH₂ | liquid | 204–205° C./0.3 mm. |
| 1,1-Dimethyl-prop-2-ynyl | 4Cl—PhCH₂ | solid | 101–103° C. |
| 2-Chloroallyl | PhCH₂ | liquid | 179–181° C./0.3 mm. |
| 2,3-Dichloro-allyl | PhCH₂ | liquid | 195–197° C./0.6 mm. |
| tert.Bu | 2,4diCl—PhCH₂ | solid | 87–88.5° C. |
| 2-Methylallyl | 2,4diCl—PhCH₂ | liquid | 188–190° C./0.3 mm. |
| s-Bu | 2,4diCl—PhCH₂ | liquid | 180–183° C./0.1 mm. |
| Hexyl | 4Cl—PhCH₂ | liquid | 185–187° C./0.08 mm. |
| tert.Bu | 4Cl—PhCH₂ | solid | 109–111° C. |
| i-Pr | 4Br—PhCH₂ | solid | 107.5–108.5° C. |
| Cyclohexyl | PhCH₂ | liquid | 130–131° C./0.15 mm. |
| Cyclohexyl | 4Cl—PhCH₂ | solid | 120–121.5° C. |
| Bu | 4Br—PhCH₂ | solid | 66.5–68° C. |
| Decyl | 4Cl—PhCH₂ | liquid | 212–215° C./0.1 mm. |
| 2-Methylallyl | 4Cl—PhCH₂ | solid | 55–57° C. |
| i-Pr | 4Me—PhCH₂ | solid | 72.5–74° C. |
| Allyl | 4Br—PhCH₂ | liquid | 194–198° C./0.2 mm. |
| Et | 2Cl—PhCH₂ | solid | 81–83° C. |
| Allyl | 2Cl—PhCH₂ | solid | 73–75° C. |
| i-Pr | 2,6diCl—PhCH₂ | solid | 132–134° C. |
| EtOCH₂CH₂ | 2,4diCl—PhCH₂ | liquid | 198–200° C./0.3 mm. |
| Bu | 4CN—PhCH₂ | solid | 102–104° C. |
| Cyclopentyl | PhCH₂ | liquid | 178–179° C./0.3 mm. |
| Pr | PhCH₂ | liquid | 165–166° C./0.4 mm. |
| EtOCH₂CH₂ | 3,4diCl—PhCH₂ | liquid | 202–204° C./0.2 mm. |
| CNCH₂CH₂ | 4Cl—PhCH₂ | solid | 103–105° C. |
| Cyclooctyl | 4Cl—PhCH₂ | solid | 95–96.5° C. |
| CNCH₂CH₂ | PhCH₂ | liquid | 202–206° C./0.05–0.1 mm. |
| PhCH₂ | 4Cl—PhCH₂ | liquid | 206–210° C./0.2 mm. |
| 4Cl—PhCH₂ | 4Cl—PhCH₂ | solid | 122–124° C. |
| PhCH₂ | 2,4diCl—PhCH₂ | solid | 109–110° C. |
| PhCH₂ | 2Cl—PhCH₂ | liquid | 225–229° C./1–1.5 mm. |
| 1,1-Dimethyl-prop-2-ynyl | 2,4diCl—PhCH₂ | solid | 107–109° C. |
| 1,1-Dimethyl-prop-2-ynyl | 4Cl—PhCH₂ | solid | 101–103° C. |
| 1,1-Dimethyl-prop-2-ynyl | 3,4diCl—PhCH₂ | solid | 109–111° C. |
| Pr | PhCH₂CH₂ | liquid | 161–163° C./0.2 mm. |
| Allyl | PhCH₂CH₂ | solid | 51–53° C. |
| Me | PhCH₂CH₂ | solid | 78.5–79.5° C. |
| i-Pr | PhCH₂CH₂ | liquid | 166° C./0.5 mm. |
| PhCH₂ | PhCH₂CH₂ | liquid | 208–210° C./0.3–0.4 mm. |
| Pr | 3MeO—PhCH₂CH₂ | liquid | 170–172° C./0.4 mm. |
| i-Pr | PhCH=CH—CH₂ | liquid | 192–194° C./0.45 mm. |
| Bu | PhCH=CH—CH₂ | liquid | 190–193° C./0.3 mm. |
| CNCH₂CH₂ | 2Cl—PhCH₂ | solid | 87° C. |
| Pr | 3MeO—PhCH₂CH₂ | liquid | 170–172° C./0.4 mm. |

-continued

| R¹ | R² | Physical State | Constant |
|---|---|---|---|
| PhC(CH₃)H | Ph(CH₂)₃ | oil | G.L.C. 99.26% |

Intermediates

The following carbamoyl chloride intermediates of general formula R¹R²NCOCl were prepared in a similar way to that described in Example 3.

| R¹ | R² | Physical State | Constant |
|---|---|---|---|
| Bu | PhCH₂ | liquid | 123–124° C./0.6 mm. |
| Cyclopentyl | 2,4diCl—PhCH₂ | solid | 68–70° C. |
| 1,1-Dimethyl-prop-2-ynyl | 4Cl—PhCH₂ | solid | 72–76° C. |
| 2-Chloroallyl | PhCH₂ | liquid | 129–131° C./1.25 mm. |
| 2,3-Dichloro-allyl | PhCH₂ | liquid | 124–126° C./0.1 mm. |
| tert.Bu | 2,4diCl—PhCH₂ | solid | 86–87° C. |
| 2-Methylallyl | 2,4diCL—PhCH₂ | liquid | 141–143° C./0.3 mm. |
| s-Bu | 2,4diCl—PhCH₂ | liquid | 122–127° C./0.1 mm. |
| Hexyl | 4Cl—PhCH₂ | liquid | 137–139° C./0.1 mm. |
| tert.Bu | 4Cl—PhCH₂ | solid | 118–119° C. |
| i-Pr | 4Br—PhCH₂ | liquid | 122–124° C./0.1 mm. |
| Cyclohexyl | PhCH₂ | liquid | 130–131° C./0.15 mm. |
| Cyclohexyl | 4Cl—PhCH₂ | liquid | 150–152° C./0.05 mm. |
| Bu | 4Br—PhCH₂ | liquid | 139–141° C./0.1 mm. |
| Decyl | 4Cl—PhCH₂ | liquid | 170–171° C./0.05 mm. |
| 2-Methylallyl | 4Cl—PhCH₂ | liquid | 122–124° C./0.05 mm. |
| i-Pr | 4Me—PhCH₂ | liquid | 103–105° C./0.12 mm. |
| Allyl | 4Br—PhCH₂ | liquid | 119–121° C./0.025 mm. |
| Et | 2Cl—PhCH₂ | liquid | 124–126° C./1.0 mm. |
| Allyl | 2Cl—PhCH₂ | liquid | 136–138° C./1.5 mm. |
| i-Pr | 2,6diCl—PhCH₂ | solid | 64–66° C. |
| EtOCH₂CH₂ | 2,4diCl—PhCH₂ | not isolated | |
| Bu | 4CN—PhCH₂ | liquid | 161–162° C./0.2 mm. |
| Cyclopentyl | PhCH₂ | liquid | 128–130° C./0.1 mm. |
| Pr | PhCH₂ | liquid | 108–109° C./0.1 mm. |
| EtOCH₂CH₂ | 3,4diCl—PhCH₂ | not isolated | |
| CNCH₂CH₂ | 4Cl—PhCH₂ | liquid | 168–172° C./0.1 mm. |
| Cyclooctyl | 4Cl—PhCH₂ | liquid | 173–175° C./0.15 mm. |
| CNCH₂CH₂ | PhCH₂ | liquid | 149–151° C./0.2 mm. |
| PhCH₂ | 4Cl—PhCH₂ | liquid | 140–142° C./0.05 mm. |
| 4Cl-PhCH₂ | 4Cl—PhCH₂ | solid | 86–87° C. |
| PhCH₂ | 2,4diCl—PhCH₂ | liquid | 186° C./0.8 mm. |
| PhCH₂ | 2Cl—PhCH₂ | liquid | 174–176° C./0.5 mm. |
| 1,1-Dimethyl prop-2-ynyl | 2,4diCl—PhCH₂ | solid | 86–88° C. |
| 1,1-Dimethyl prop-2-ynyl | 4Cl—PhCH₂ | solid | 72–74° C. |
| 1,1-Dimethyl-prop-2-ynyl | 3,4diCl—PhCH₂ | solid | 86–88° C. |
| Pr | PhCH₂CH₂ | liquid | 128–130° C./0.2 mm. |
| Allyl | PhCH₂CH₂ | liquid | 116–118° C./0.2 mm. |
| Me | PhCH₂CH₂ | solid | 51–52.5 ° C. |
| i-Pr | PhCH₂CH₂ | liquid | 124–125° C./0.4 mm. |
| PhCH₂ | PhCH₂CH₂ | solid | 56–58° C. |
| Pr | 3MeO—PhCH₂CH₂ | liquid | 143° C./0.45 mm. |
| i-Pr | PhCH=CH—CH₂ | not isolated | |
| Bu | PhCH=CH—CH₂ | not isolated | |
| CNCH₂CH₂ | 2Cl—PhCH₂ | liquid | 161–164° C./0.25 mm. |
| Pr | 3MeO—PhCH₂CH₂ | liquid | 143° C./0.45 mm. |
| PhC(CH₃)H | Ph(CH₂)₃ | not isolated | |

EXAMPLE 5

This example illustrates the preparation of compounds according to the invention.

12.4 g. N-2-chlorophenyl-N-propyl(thiocarbamoyl) chloride and 6.8 g. imidazole were refluxed in 75 ml. dry tetrahydrofuran for 16 hours. A further 2 g. imidazole was then added and the heating continued for 8 hours. After separating the solid formed evaporation of the tetrahydrofuran left an oil which was dissolved in methylene chloride. The resulting organic phase was washed with water, dried with soldium sulphate and the solvent evaporated to leave an oil which crystallised on treatment with light petroleum and chilling to give the product, 1-[N-2-chlorophenyl-N-propyl (thiocarbamoyl)]imidazole, m.p. 59°–61° C.

The N-2-chlorophenyl-N-propyl(thiocarbamoyl)-chloride reactant was prepared in the following way.

A solution of 25.4 g. 2-chloro-N-propylaniline and 15.15 g. dry triethylamine in 200 ml. dry ether was added to a solution of 13 ml. thiophosgene in 200 ml. of the same solvent at −20° C. The reaction mixture was allowed to warm to room temperature and then filtered, the filtered solid being washed with ether. The ethereal extract was added to the ethereal liquor and after drying over sodium sulphate, was evaporated to give a dark oil. On standing further solid precipitated, which was then separated from the oil. The oily filtrate was distilled to give the product N-2-chlorophenyl-N-propyl(thiocarbamoyl) chloride, b.p. 119°–120° C./0.4 mm. Hg.

The following thiocarbamoylimidazole compounds of general formula I (X=sulphur) were prepared in a similar manner. Crude liquids were distilled under vacuum to give the pure product.

Compounds of the Invention

| $R^1$ | $R^2$ | Physical State | Constant |
|---|---|---|---|
| Me | Ph | liquid | 139–141° C./0.1 mm. |
| Me | 4Me—Ph | solid | 88–89° C. |
| Me | 4MeO—Ph | liquid | 166–167° C./0.15 mm. |
| Et | 4Cl—Ph | solid | 69.5–71° C. |
| Et | 2Cl—Ph | solid | 72.5–74° C. |
| Pr | 4Cl—Ph | solid | 87–89° C. |
| i-Pr | 2,4diCl—PhCH$_2$ | solid | 130–131.5° C. |
| Hexyl | 4Cl—Ph | solid | 54.5–56.5° C. |
| CNCH$_2$CH$_2$ | 4Cl—Ph | solid | 104.5–106° C. |
| Pr | 2Cl—PhCH$_2$ | solid | 75.5–77° C. |
| Allyl | 4Cl—PhCH$_2$ | solid | 62.5–63.5° C. |
| Et | 2,4diCl—Ph | solid | 89.5–91.5° C. |
| i-Pr | 4Cl—PhCH$_2$ | solid | 119–120.5° C. |

Intermediates

The following thiocarbamoyl chloride intermediates of general formula $R^1R^2NCSCl$ were prepared in a similar way to the method described above for the preparation of N-2-chlorophenyl-N-propyl(thiocarbamoyl) chloride.

| $R^1$ | $R^2$ | Physical State | Constant |
|---|---|---|---|
| Me | Ph | liquid | 137–139° C./4.5 mm. |
| Me | 4Me—Ph | solid | 58–59.5° C. |
| Me | 4MeOPh | liquid | 166–167° C./0.15 mm. |
| Et | 4Cl—Ph | liquid | 103–104° C./0.05 mm. |
| Et | 2Cl—Ph | liquid | 102–104° C./0.1 mm. |
| Pr | 4Cl—Ph | liquid | 118° C./0.1 mm. |
| i-Pr | 2,4diCl—PhCH$_2$ | liquid | 156–158° C./0.5 mm. |
| Hexyl | 4Cl—Ph | solid | 45.5–47° C. |
| CNCH$_2$CH$_2$ | 4Cl—Ph | solid | 118.5–120.5° C. |
| Pr | 2Cl—PhCH$_2$ | solid | 47–48.5° C. |
| Allyl | 4Cl—PhCH$_2$ | liquid | 145–148° C./0.15 mm. |
| Et | 2,4diCl—Ph | liquid | 124–127° C./0.3 mm. |
| i-Pr | 4Cl—PhCH$_2$ | solid | 88.5–90° C. |

EXAMPLE 6

This example illustrates the preparation of 1-(N-2-phenoxyethyl-N-propylcarbamoyl) imidazole and related imidazoles of the invention.

To 75 ml. dry tetrahydrofuran were added 6.8 g. imidazole and 12.075 g. N-2-phenoxyethyl-N-propyl-carbamoyl chloride. The reactants were boiled together under reflux for 24 hours, cooled to room temperature and filtered to remove imidazole hydrochloride. The solvent was then removed by evaporation from the steam bath, the last traces being removed under vacuum. An oily residue remained which was extracted into ether, washed with water, dried over anhydrous sodium sulphate, the solvent removed and the residual oil distilled under vacuum, to give 1-(N-2-phenoxyethyl-N-propylcarbamoyl) imidazole, boiling point 209° C./1.0 mm.

The N-2-phenoxyethyl-N-propylcarbamoyl chloride was prepared in the following way.

47.2 g. Propylamine was dissolved in 100 ml. absolute alcohol with cooling and 40.2 g. β-bromophenetole was added portionwise to the solution formed. After completion of the addition the reaction mixture was allowed to stand at room temperature for 1 week with occasional agitation. The excess of amine and solvent were then removed under vacuum from the steam bath and the residual colourless solid obtained on cooling was treated with an excess of 5N aqueous sodium hydroxide. An oil was liberated which was then extracted with ether, washed with water and dried over anhydrous sodium sulphate. After removal of the solvent the residual oil was distilled under vacuum to give N-2-phenoxyethyl-N-propylamine, boiling point 90°–92° C./0.2 mm.

To 100 ml. of mechanically stirred, refluxing dry ethyl acetate was introduced a steady flow of phosgene gas followed by the dropwise addition of 22.4g. N-2-phenoxyethyl-N-propylamine in 100 ml. dry ethyl acetate over a period of 45 minutes. On completion of the addition, the reaction mixture was boiled under reflux with stirring, whilst continuing the flow of phosgene for a further three hours. The solvent was removed on the steam bath, the last traces being extracted under vacuum to give N-2-phenoxyethyl-N-propylcarbamoyl chloride.

The following carbamoylimidazole compounds of general formula I (X=oxygen) were prepared in a similar manner. Solid compounds were recrystallised from a suitable solvent such as light petroleum to give the pure product.

Compounds of the Invention.

| $R^1$ | $R^2$ | Physical State | Constant |
|---|---|---|---|
| s-Bu | PhOCH$_2$CH$_2$ | solid | 63.5–65° C. |
| i-Pr | PhOCH$_2$CH$_2$ | liquid | 177–179° C./0.2 mm. |
| PhCH$_2$ | PhOCH$_2$CH$_2$ | solid | 106–108° C. |
| PhCH$_2$ | 4Cl—PhOCH$_2$CH$_2$ | solid | 93–95° C. |
| 2Cl—PhCH$_2$ | 4Cl—PhOCH$_2$CH$_2$ | solid | 76–78° C. |
| Me | PhOCH$_2$CH$_2$ | liquid | 186–188° C./0.15 mm. |
| i-Bu | PhOCH$_2$CH$_2$ | solid | 80.5–82° C. |
| Pr | 4Cl—PhOCH$_2$CH$_2$ | solid | 70.5–72° C. |
| Bu | PhOCH$_2$CH$_2$ | solid | 46–48° C. |
| PhCH$_2$ | 2Cl—PhOCH$_2$CH$_2$ | solid | 110–112° C. |
| Pentyl | PhOCH$_2$CH$_2$ | solid | 51–52.5° C. |
| Hexyl | PhOCH$_2$CH$_2$ | solid | 40–41.5° C. |
| Pr | 2Me—PhOCH$_2$CH$_2$ | liquid | 186–188° C./0.2 mm. |
| Pr | 2Cl—PhOCH$_2$CH$_2$ | solid | 57–58.5° C. |
| Pr | 4Me—PhOCH$_2$CH$_2$ | solid | 65.5–67° C. |
| Pr | 3Cl—PhOCH$_2$CH$_2$ | solid | 37–39° C. |
| 4Cl—PhCH$_2$ | 2,4diCl—PhOCH$_2$—CH$_2$ | solid | 128–130° C. |
| PhCH$_2$ | 3,4diCl—PhOCH$_2$—CH$_2$ | solid | 128.6° C. |
| Octyl | PhOCH$_2$CH$_2$ | liquid | 15° C. |

-continued
Compounds of the Invention.

| R¹ | R² | Physical State | Constant |
|---|---|---|---|
| Pr | PhO(CH₂)₃ | liquid | 198–199° C./0.4 mm. |
| Bu | PhO(CH₂)₃ | liquid | 193–194° C./0.2 mm. |
| PhCH₂ | 2Me—4Cl—PhOCH₂—CH₂ | solid | 114–116° C. |
| PhC(CH₃)H | 4Cl—PhOCH₂CH₂ | liquid | 215–220° C./0.1–0.2 mm. |
| PhCH₂ | 4Br—PhOCH₂CH₂ | solid | 101–103° C. |
| Pr | 2Me—4Cl—PhOCH₂—CH₂ | solid | 79.5–81° C. |
| Bu | 2Cl-PhOCH₂CH₂ | solid | 64–65.5° C. |
| Pr | PhSCH₂CH₂ | liquid | 189° C./0.2 mm. |
| PhCH₂CH₂ | PhOCH₂CH₂ | solid | 73–75° C. |
| PhCH₂ | 2,4diMe—PhOCH₂—CH₂ | solid | 121–123° C. |
| Pr | 3,4diCl—PhOCH₂—CH₂ | solid | 84.5–86° C. |
| 2Cl—Ph | PhOCH₂CH₂ | solid | 80.5–82.5° C. |
| Prop-2-ynyl | PhOCH₂CH₂ | solid | 76–78° C. |
| Ph | 4Cl—PhOCH₂CH₂ | solid | 86–88° C. |
| Allyl | PhOCH₂CH₂ | liquid | 186–190° C./0.4 mm. |
| Allyl | 4Cl—PhOCH₂CH₂ | solid | 53–55° C. |
| PhCH₂ | 2,4diCl—PhO(CH₂)₃ | solid | 87–89° C. |
| PhCH₂ | 2,4,5triCl—PhOCH₂—CH₂ | solid | 135–137° C. |
| PhCH₂ | 4Cl—PhSCH₂CH₂ | solid | 84–86° C. |
| PhCH₂ | 4MeO—PhOCH₂CH₂ | solid | 107° C. |
| Pr | 4Br—PhOCH₂CH₂ | solid | 73–74.5° C. |
| i-Bu | 4Cl—PhOCH₂CH₂ | solid | 89.5–91° C. |
| Bu | 4Cl—PhOCH₂CH₂ | solid | 53.5–54.5° C. |
| i-Pr | 4Cl—PhOCH₂CH₂ | solid | 57.5–59° C. |
| Pr | 3CF₃—PhOCH₂CH₂ | solid | 63–64.5° C. |
| i-Bu | PhO(CH₂)₃ | liquid | 188–190° C./0.15 mm. |
| PhCH₂ | 2Ph—PhOCH₂CH₂ | solid | 96–98° C. |
| Pr | 2,4,6-triCl—PhOCH₂CH₂ | liquid | 208–210° C./0.2 mm. |
| Pr | 4Cl—PhO(CH₂)₃ | liquid | 206–208/0.2 mm. |
| Bu | 4Cl—PhO(CH₂)₃ | liquid | 212–214° C./0.2 mm. |
| Pr | 2Br—PhOCH₂CH₂ | solid | 65–66.5° C. |
| i-Pr | PhSCH₂CH₂ | solid | 70.5–71.5° C. |
| Pr | 4Me—PhSCH₂CH₂ | solid | 63.5–65° C. |
| Pr | 3CF₃—PhSCH₂CH₂ | liquid | 186–188° C./0.3 mm. |
| Pr | 2,4,5triCl—PhOCH₂CH₂ | solid | 77–78.5° C. |
| Pr | 4Cl—PhSCH₂CH₂ | solid | 45.5–47.5° C. |
| PhCH₂ | 2Br—PhOCH₂CH₂ | solid | 116° C. |
| Pr | 2Cl—PhO(CH₂)₃ | liquid | 204–209° C./0.2–0.25 mm. |
| PhCH₂ | 2,4,6triCl—PhO(CH₂)₃ | oil | G.L.C. 95.33% |
| PhCH₂ | PhSCH₂CH₂ | oil | G.L.C. 97.65% |
| PhCH₂ | 4Cl—PhO(CH₂)₃ | oil | G.L.C. 98.56% |
| PhCH₂CH₂ | 4Cl—PhOCH₂CH₂ | oil | G.L.C. 99.35% |
| PhCH₂ | 3CF₃—PhSCH₂CH₂ | oil | G.L.C. 96.62% |

Intermediates

Carbamoyl chloride intermediates were prepared in a similar way to that described above for the preparation of N-2-phenoxyethyl-N-propylcarbamoyl chloride. The carbamoyl chlorides were not purified but were used directly in the carbamoylation of imidazole to give the carbamoylimidazoles listed above. The following table lists the carbamoyl chloride intermediates and the amines from which they were derived. These latter compounds, all of which were liquids, were isolated and characterised.

TABLE

| Carbamoyl Chloride Intermediates R¹R²NCOCL | | Amine Intermediates R¹R²NH |
|---|---|---|
| R¹ | R² | boiling point |
| s-Bu | PhOCH₂CH₂ | 122–125° C./6.5 mm. |
| i-Pr | PhOCH₂CH₂ | 109–111° C./6.5 mm. |
| PhCH₂ | PhOCH₂CH₂ | 141–143° C./0.3 mm. |
| PhCH₂ | 4Cl—PhOCH₂CH₂ | 158–162° C./0.4 mm. |
| 2Cl—PhCH₂ | 4Cl—PhOCH₂CH₂ | 159–162° C./0.1 mm. |
| Me | PhOCH₂CH₂ | 102–105° C./8.0 mm. |
| i-Bu | PhOCH₂CH₂ | 107–108° C./2.5 mm. |
| Pr | 4Cl—PhOCH₂CH₂ | 145–147° C./6.0 mm. |
| Bu | PhOCH₂CH₂ | 115–117° C./2.5 mm. |
| PhCH₂ | 2Cl—PhOCH₂CH₂ | 155–162° C./0.3–0.4 mm. |
| Pentyl | PhOCH₂CH₂ | 110–113° C./0.5 mm. |
| Hexyl | PhOCH₂CH₂ | 130–132° C./0.5 mm. |
| Pr | 2Me—PhOCH₂CH₂ | 88–91° C./0.7 mm. |
| Pr | 2Cl—PhOCH₂CH₂ | 104–106° C./0.6 mm. |
| Pr | 4Me—PhOCH₂CH₂ | 90–93° C./0.2 mm. |
| Pr | 3Cl—PhOCH₂CH₂ | 106–108° C./0.4 mm. |
| 4Cl—PhCH₂ | 2,4diCl—PhOCH₂CH₂ | 176–182° C./0.1 mm. |
| PhCH₂ | 3,4diCl—PhOCH₂CH₂ | 200–203° C./1.5 mm. |
| Octyl | PhOCH₂CH₂ | 130–133° C./0.3 mm. |

TABLE-continued

| Carbamoyl Chloride Intermediates R¹R²NCOCL | | Amine Intermediates R¹R²NH |
|---|---|---|
| R¹ | R² | boiling point |
| Pr | PhO(CH₂)₃ | 163–166° C./30 mm. |
| Bu | PhO(CH₂)₃ | 106–108° C./0.3 mm |
| PhCH₂ | 2Me—4Cl—PhOCH₂CH₂ | 159–161° C./0.2 mm. |
| PhC(CH₃)H | 4Cl—PhOCH₂CH₂ | 145–148° C./0.2 mm. |
| PhCH₂ | 4Br—PhOCH₂CH₂ | 169–171° C./0.3 mm. |
| Pr | 2Me—4Cl—PhOCH₂CH₂ | 138–139° C./3.0 mm. |
| Bu | 2Cl—PhOCH₂CH₂ | 120–122° C./1.5 mm. |
| Pr | PhSCH₂CH₂ | 124–126° C./3.0 mm. |
| PhCH₂CH₂ | PhOCH₂CH₂ | 128–130° C./0.02 mm. |
| PhCH₂ | 2,4diMe—PhOCH₂CH₂ | 167–170° C./0.8 mm. |
| Pr | 3,4diCl—PhOCH₂CH₂ | 114–116° C./0.15 mm. |
| 2Cl—Ph | PhOCH₂CH₂ | 149–153° C./0.1 mm. |
| Prop-2-ynyl | PhOCH₂CH₂ | 89° C./0.2 mm. |
| Ph | 4Cl—PhOCH₂CH₂ | 155–157° C./0.2 mm. |
| Allyl | PhOCH₂CH₂ | 109–110° C./3.5 mm. |
| Allyl | 4Cl—PhOCH₂CH₂ | 129–131° C./2.6 mm. |
| PhCH₂ | 2,4diCl—PhO(CH₂)₃ | 184–186° C./0.3 mm. |
| PhCH₂ | 2,4,5triCl—PhOCH₂CH₂ | 180–182° C./0.2–0.25 mm. |
| PhCH₂ | 4Cl—PhSCH₂CH₂ | 170–173° C./0.3 mm. |
| PhCH₂ | 4MeO—PhOCH₂CH₂ | 157–160° C./0.1 mm. |
| Pr | 4Br—PhOCH₂CH₂ | 142–143° C./2.75 mm. |
| i-Bu | 4Cl—PhOCH₂CH₂ | 93–96° C./0.15 mm. |
| Bu | 4Cl—PhOCH₂CH₂ | 112–115° C./0.2 mm. |
| i-Pr | 4Cl—PhOCH₂CH₂ | 96–99° C./0.1 mm. |
| Pr | 3CF₃—PhOCH₂CH₂ | 88–90° C./2.0 mm. |
| i-Bu | PhO(CH₂)₃ | 110–113° C./1.75 mm. |
| PhCH₂ | 2Ph—PhOCH₂CH₂ | 188° C./0.3 mm. |
| Pr | 2,4,6triCl—PhOCH₂CH₂ | 112–114° C./0.2 mm. |
| Pr | 4Cl—PhO(CH₂)₃ | 105–107° C./0.2 mm. |
| Bu | 4Cl—PhO(CH₂)₃ | 113–115° C./0.25 mm. |
| Pr | 2Br—PhOCH₂CH₂ | 97–100° C./0.2 mm. |
| i-Pr | PhSCH₂CH₂ | 93–95° C./0.8 mm. |
| Pr | 4Me—PhSCH₂CH₂ | 112–114° C./0.9 mm. |
| Pr | 3CF₃—PhSCH₂CH₂ | 104–106° C./13 mm. |
| Pr | 2,4,5triCl—PhOCH₂CH₂ | 125–126° C./0.2 mm. |
| Pr | 4Cl—PhSCH₂CH₂ | 143–144° C./2.5 mm. |
| PhCH₂ | 2Br—PhOCH₂CH₂ | 154° C./0.1 mm. |
| Pr | 2Cl—PhO(CH₂)₃ | 111° C./0.4 mm. |
| PhCH₂ | 2,4,6triCl—PhO(CH₂)₃ | 165–169° C./0.1 mm. |
| PhCH₂ | PhSCH₂CH₂ | 134–138° C./0.05–0.1 mm. |
| PhCH₂ | 4Cl—PhO(CH₂)₃ | 164° C./0.2 mm. |
| PhCH₂CH₂ | 4Cl—PhOCH₂CH₂ | 160–161° C./0.2 mm. |
| PhCH₂ | 3CF₃—PhSCH₂CH₂ | 122–125° C./0.05 mm. |

EXAMPLE 7

This example illustrates an alternative method of preparing the imidazole compounds of the invention by reacting carbonylbisimidazole with an appropriate secondary amine.

Dry benzene was distilled from calcium dihydride into a flask containing 27.2 g. imidazole which on gentle warming dissolved in the solvent. 9.5 ml. Phosgene was collected by means of a dry-ice condenser and transferred into the warm benzene solution by hand through a drying train. The drying train was then flushed with dry nitrogen and, finally, excess of phosgene was removed from the benzene by direct blowing of the dry gas. After stirring for 2 hours a lower layer of imidazole hydrochloride separated. The mixture was heated to 50° C., allowed to cool and the benzene layer decanted from the oil produced.

16.5 g. N-4-chlorobenzyl-N-isopropylamine was added and the mixture heated under reflux for 48 hours. The benzene was then evaporated and the residue dissolved in ether, washed with water, and dried over sodium sulphate. Evaporation gave an oil which was dissolved in light petroleum (40°–60° C.) and after seeding and chilling a white solid precipitated, 1-(N-4-chlorobenzyl-N-isopropylcarbamoyl)imidazole, m.p. 120°–121.5° C.

EXAMPLE 8

This example illustrates an emulsifiable concentrate according to the invention.

An emulsifiable concentrate suitable for dilution with water to form an aqueous emulsion was prepared from the following ingredients:

| | |
|---|---|
| 1-(N-2,4-dichlorophenyl-N-ethylcarbamoyl)imidazole | 25.0% w/v |
| Calcium dodecylbenzenesulphonate | 2.5% w/v |
| Nonylphenoxypolyethoxyethanol* | 2.5% w/v |
| Xylene | to 100.0% volume |

*A nonylphenol-ethylene oxide condensate containing an average of 14 mols. ethylene oxide per mol. nonylphenol.

EXAMPLE 9

This example illustrates a granular composition of the invention.

Granules containing 5% w/w of 1-(N-2,4-dichlorophenyl-N-ethylcarbamoyl)imidazole and 5% w/w paraffin wax were prepared by first impregnating granules of fuller's earth (mesh size 22/44 British Standard Sieve) with a solution of the imidazole compound in xylene and then evaporating the xylene from the impregnated granules. The granules were then treated with a xylene solution of the paraffin wax and the solvent evaporated to give a surface coating of wax.

EXAMPLE 10

This example illustrates a seed dressing composition according to the invention.

A seed dressing composition was prepared by mixing together the following ingredients.

| | |
|---|---|
| 1-(N-2,4-dichlorophenyl-N-ethylcarbamoyl) imidazole | 15.0% w/w |
| Colloidal silicic acid | 25.0% w/w |
| Talc | 10.0% w/w |
| Gypsum powder | 50.0% w/w |

EXAMPLE 11

This example illustrates a dispersible powder according to the invention.

A dispersible powder was prepared from the following ingredients.

| | |
|---|---|
| 1-(N-2-chlorophenyl-N-propylcarbamoyl) imidazole | 25.0% w/w |
| Ethylan MR* | 1.0% w/w |
| Dyapol PT** | 5.0% w/w |
| Kaolin | 69.0% w/w |

*An alkylphenol ethoxylate.
**A sulphonated condensate of urea, cresol and formaldehyde.

EXAMPLE 12

This example illustrates the fungicidal acitivity of compounds of the invention when used to control mildew on oats.

In one set of experiments oat seedlings were infected with the cereal powdery mildew, Erysiphe graminis, and subsequently sprayed with a suspension or solution of test compound at 2000 parts per million.

In a further set of experiments oat seedlings were first sprayed with the suspension or solution of test compound at a cencentration of 2000 parts per million and the treated seedlings then inoculated with powdery mildew.

A visual assessment was made of the infection, if any, that resulted from both of these tests. The following compounds were found to give greater than 70 percent control of mildew in both tests.

1-(N-2,4-dichlorophenyl-N-ethylcarbamoyl)imidazole
1-(N-2,4-dichlorophenyl-N-pentylcarbamoyl)imidazole
1-(N-4-chlorophenyl-N-sec.butylcarbamoyl)imidazole
1-(N-2-chloro-4-nitrophenyl-N-propylcarbamoyl)imidazole
1-(N-2,4-dichlorobenzyl-N-isopropylcarbamoyl)imidazole
1-[N-2,4-dichlorobenzyl-N-(1,1-dimethylprop-2-ynyl)carbamoyl] imidazole
1-(N-4-chlorobenzyl-N-tert.butylcarbamoyl)imidazole
1-(N-4-chlorobenzyl-N-2,4-dichlorophenylcarbamoyl)imidazole
1-(N,N-bis-4-chlorobenzylcarbamoyl)imidazole
1-(N-2,4-dichlorobenzyl-N-sec.butylcarbamoyl)imidazole
1-(N-4-chlorobenzyl-N-cyclooctylcarbamoyl)imidazole
1-(N-benzyl-N-2,4-dichlorophenylcarbamoyl)imidazole
1-(N-benzyl-N-2-phenethylcarbamoyl)imidazole
1-(N-benzyl-N-2-phenoxyethylcarbamoyl)imidazole
1-(N-benzyl-N-2-p-chlorophenoxyethylcarbamoyl)imidazole
1-(N-benzyl-N-2-o-chlorophenoxyethylcarbamoyl)imidazole
1-(N-2-chlorobenzyl-N-2-p-chlorophenoxyethylcarbamoyl)imidazole
1-(N-2-chlorobenzyl-N-2-phenethylcarbamoyl)imidazole
1-(N-2,4-dichlorobenzyl-N-2-chlorophenylcarbamoyl)imidazole
1-(N,N-bis-phenylcarbamoyl)imidazole

EXAMPLE 13

This example illustrates the fungicidal activity of compounds of the invention when used to control mildew on oats.

A weighed quantity of imidazole compound was thoroughly mixed with a weighed quantity of soil so as to give a mixture containing 250 parts per million of the compound. Oat seeds were then sown in pots containing the soil mixtures and the resulting seedlings infected with the cereal powdery mildew, Erysiphe graminis. A visual assessment was later made in order to determine whether the powdery mildew had taken hold. There was greater than 70 percent control of mildew on plants that had been grown in soil treated with the following inidazole compounds.

1-(N-2,4-dichlorophenyl-N-ethylcarbamoyl)imidazole
1-(N-2,4-dichlorophenyl-N-methylcarbamoyl)imidazole
1-(N-2-fluorophenyl-N-propylcarbamoyl)imidazole
1-(N-2-chlorophenyl-N-propylcarbamoyl)imidazole
1(N-4-chlorophenyl-N-propylcarbamoyl)imidazole
1-(N-2,4-dichlorophenyl-N-propylcarbamoyl)imidazole
1-(N-4-chlorophenyl-N-sec.butylcarbamoyl)imidazole
1-(N-2-chlorophenyl-N-isopropylcarbamoyl)imidazole
1-(N-2,4,5-trichlorophenyl-N-ethylcarbamoyl)imidazole
1-(N-4-cyanophenyl-N-ethylcarbamoyl)imidazole
1-(N-4-chlorobenzyl-N-allylcarbamoyl)imidazole
1-(N-4-fluorophenyl-N-propylcarbamoyl)imidazole
1-(N-2-methyl-4-chlorophenyl-N-butylcarbamoyl)imidazole

EXAMPLE 14

This example illustrates the activity of compounds of the invention when used to control mildew on barley.

A field of barley at about growth stage five and naturally infected with mildew (Erysiphe graminis) was divided into plots. Aqueous sprays containing the active ingredient were applied to the barley at a rate of 1 pound active ingredient per acre in 40 gallons of liquid. Three replicate plots were sprayed in this way and control plots were left untreated for comparative purposes.

Nine days after spraying the treated and untreated plots were assessed visually and the percentage control in the treated plots was calculated with respect to the untreated plots. All of the following compounds gave an average of at least 60 percent control.

1-(N-4-chlorophenyl-N-propylcarbamoyl)imidazole
1-(N-2-chlorophenyl-N-propylcarbamoyl)imidazole
1-(N-2-fluorophenyl-N-propylcarbamoyl)imidazole
1-(N-4-chlorophenyl-N-propylthiocarbamoyl)imidazole
1-(N-2,4-dichlorophenyl-N-ethylcarbamoyl)imidazole
1-(N-2,4-dichlorophenyl-N-methylcarbamoyl)imidazole

EXAMPLE 15

This example illustrates the activity of compounds of the invention in controlling mildew on marrows.

A field of marrows (hybrid Zucchini) infected with mildew (Sphaerotheca fuliginea) was divided into plots. Aqueous sprays prepared from emulsifiable concentrates of the kind described in example 8 containing the active ingredients listed below were sprayed on to the plots when mildew was first observed. The spray contained 0.05% by weight of active ingredient and was applied to run off.

An assessment was made of control of mildew 1 week later by comparing the incidence of infection in treated plots and untreated plots.

The following compounds were found to give an average of at least 60 percent control of mildew:

1-(N-4-chlorophenyl-N-propylthiocarbamoyl)imidazole
1-(N-2,4-dichlorophenyl-N-ethylcarbamoyl)imidazole
1-(N-4-chlorophenyl-N-pentylcarbamoyl)imidazole

EXAMPLE 16

This example illustrates the activity of compounds of the invention in controlling Botrytis cinerea.

A quantity of agar containing 2 percent malt extract was sterilised in an antoclave. 20 ml. of the material was dispensed into a boiling tube containing sufficient of the active compound to give a concentration of 10 parts per million, after stirring to ensure uniform distribution. The contents of the boiling tube were then poured into a Petri dish and allowed to solidify. A spore suspension in sterile distilled water was prepared and the agar inoculated with it. After incubating the agar for a period of 1 week it was examined to assess the growth of the fungus and compared with control experiments in which the active compound had been omitted from the agar medium. The percentage reduction in area compared with the control was calculated.

The following compounds gave a percentage reduction of greater than 75 against Botrytis cinerea.

1-(N-hexyl-N-2-phenoxyethylcarbamoyl)imidazole
1-(N-pentyl-N-2-phenoxyethylcarbamoyl)imidazole
1-[-N-propyl-N-2-(2,4,6-trichlorophenoxy)ethylcarbamoyl]imidazole
1-[N-isopropyl-N-2-(4-chlorophenoxy)ethylcarbamoyl]imidazole
1-[N-2-phenethyl-N-3-(4-chlorophenoxy)propylcarbamoyl]imidazole
1-(N-sec.butyl-N-2-phenoxyethylcarbamoyl)imidazole
1-(N-butyl-N-2-phenoxyethylcarbamoyl)imidazole

What is claimed is:
1. A compound of the formula

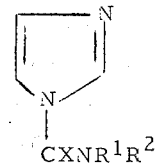

in which X is oxygen or sulphur, $R^1$ is selected from the group consisting of alkyl of 1 to 10 carbon atoms, alkenyl of 3 or 4 carbon atoms, alkynyl of 3 to 5 carbon atoms, cycloalkyl of 3 to 10 carbon atoms, optionally substituted phenyl, phenylalkyl of the formula Ph$(CH_2)_n$ where $n$ is 1 to 5, phenylalkenyl of 9 to 11 carbon atoms, phenoxyalkyl of the formula PhO$(CH_2)_n$ where $n$ is 2 to 5 and phenylthioalkyl of the formula PhS$(CH_2)_n$ where $n$ is 2 to 5, wherein the substituted phenyl nucleus has at least one substituent selected from the group consisting of halo, alkoxy of 1 or 2 carbon atoms, alkyl of 1 to 4 carbon atoms, trihalomethyl, cyano, methylthio, nitro and methylsulphonyl, and $R^2$ is selected from the group consisting of optionally substituted phenylalkyl of the formula Ph$(CH_2)_n$ where $n$ is 1 to 5, phenylalkenyl of 9 to 11 carbon atoms, phenoxyalkyl of the formula PhO$(CH_2)_n$ where $n$ is 2 to 5 and phenylthioalkyl of the formula PhS$(CH_2)_n$ where $n$ is 2 to 5, wherein the substituted phenyl nucleus has at least one substituent selected from the group consisting of halo, alkoxy of 1 or 2 carbon atoms, alkyl of 1 to 4 carbon atoms, trihalomethyl, cyano, methylthio, nitro and methylsulphonyl.

2. A compound according to claim 1 wherein X is oxygen.

3. A compound according to claim 2 in which $R^1$ is selected from the group consisting of alkyl of 1 to 10 carbon atoms, optionally substituted phenyl, benzyl and phenethyl, wherein the substituted phenyl nucleus has 1 to 3 substituents selected from the group consisting of halo, alkoxy of 1 or 2 carbon atoms, alkyl of 1 to 4 carbon atoms, trihalomethyl, cyano, methylthio, nitro and methylsulphonyl and in which $R^2$ is optionally substituted phenoxyalkyl of the formula PhO $(CH_2)_n$ where $n$ is 2 to 5 and wherein the substituted phenyl nucleus has 1 to 3 substituents selected from the group consisting of halo, alkoxy of 1 or 2 carbon atoms, alkyl of 1 to 4 carbon atoms, trihalomethyl, cyano, methylthio, nitro and methylsulphonyl.

4. A compound according to claim 3 in which the optionally substituted phenoxyalkyl group is optionally substituted 2-phenoxyethyl.

5. A compound according to claim 1 in which $R^1$ is alkyl of 1 to 6 carbon atoms and $R^2$ is 2-phenoxyethyl optionally substituted with 1 to 3 substituents selected from the group consisting of halo, methoxy, methyl and trihalomethyl.

6. A compound according to claim 1 in which $R^1$ is alkyl of 1 to 6 carbon atoms.

7. A compound according to claim 2 in which $R^1$ is alkyl containing 1 to 4 carbon atoms and $R^2$ is benzyl substituted with 1 or 2 halo atoms.

* * * * *